Figure 3:
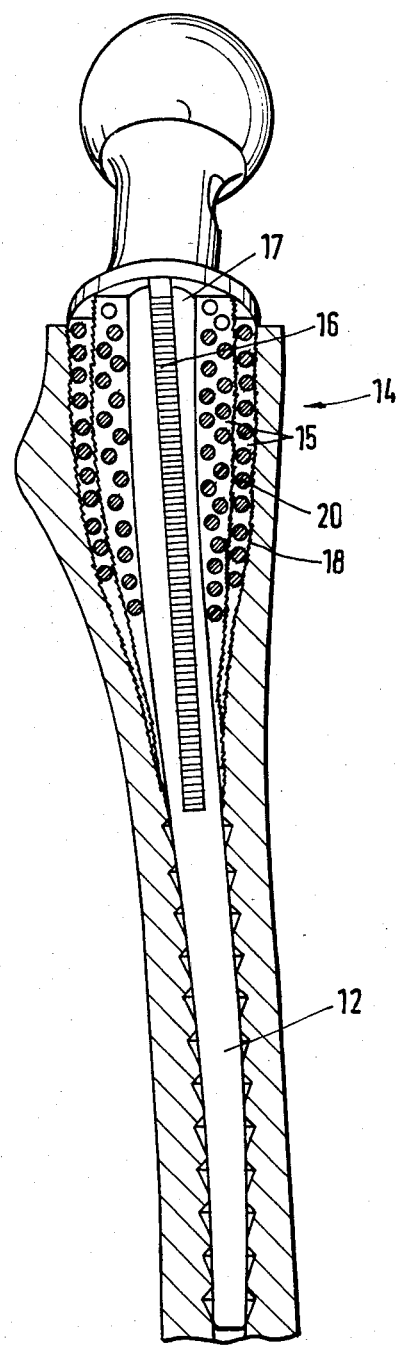

United States Patent [19]
Keller

[11] Patent Number: 4,608,053
[45] Date of Patent: Aug. 26, 1986

[54] FEMORAL HIP PROSTHESIS

[75] Inventor: Arnold Keller, Kayhude, Fed. Rep. of Germany

[73] Assignee: Waldemar Link GmbH & Co., Hamburg, Fed. Rep. of Germany

[21] Appl. No.: 490,008

[22] Filed: Apr. 29, 1983

[30] Foreign Application Priority Data

May 3, 1982 [DE] Fed. Rep. of Germany ....... 3216539

[51] Int. Cl.⁴ .................................................. A61F 2/32
[52] U.S. Cl. .................................... 623/23; 128/92 C
[58] Field of Search .................. 3/1.9, 1.91, 1.911, 3/1.912, 1.913; 128/92 C

[56] References Cited
FOREIGN PATENT DOCUMENTS 837294 5/1952 Fed. Rep. of Germany.
2933229 3/1981 Fed. Rep. of Germany ....... 3/1.912
1278359 10/1961 France.

Primary Examiner—Richard J. Apley
Assistant Examiner—David Isabella
Attorney, Agent, or Firm—Townsend and Townsend

[57] ABSTRACT

A femoral hip joint prosthesis with a stem (6) which is intended for anchorage without cement in the femur (1) and the proximal end section of which, in order to substantially fill the spongy part of the femur, is greatly thickened in the trochanteric region (14) thereof, as compared with its distal section (12), comprises a thickening which is made in the form of a plurality of longitudinal ribs (15) which project from a slender stem core (17) on the dorsal and ventral sides thereof and which face the medial side with a broad surface and have a multiplicity of perforations (20) which are substantially closed towards the ridge (18) of the rib. As a result, the conditions for the transmission of forces to the bone tissue in the proximal end section of the prosthesis stem are improved, it being possible at the same time to exert a favorable influence on the elasticity of the stem.

22 Claims, 10 Drawing Figures

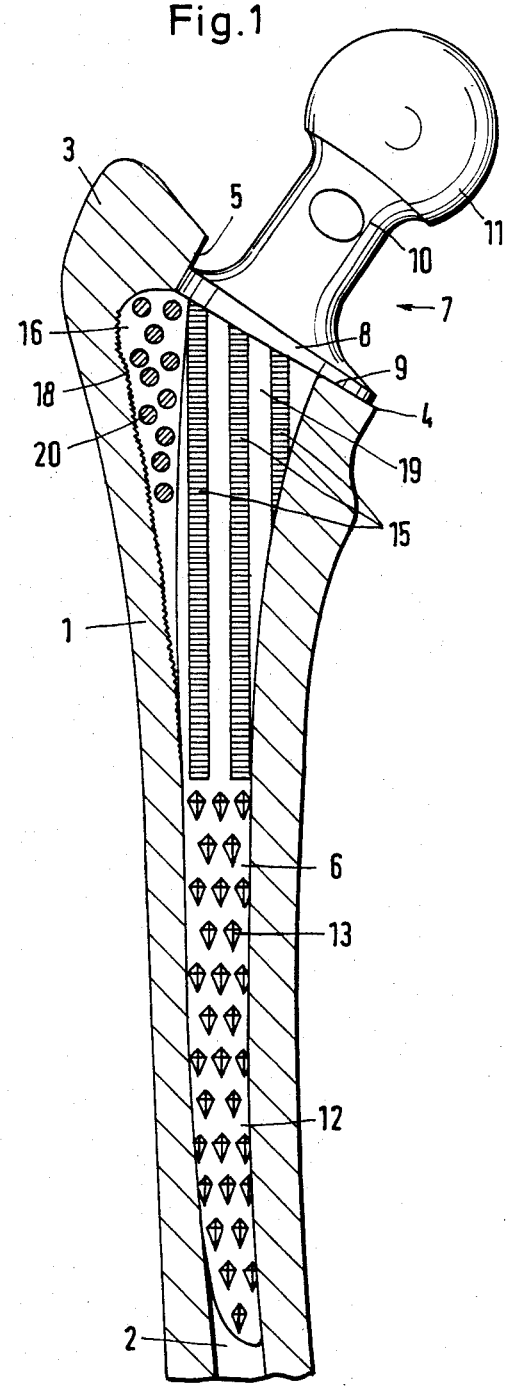
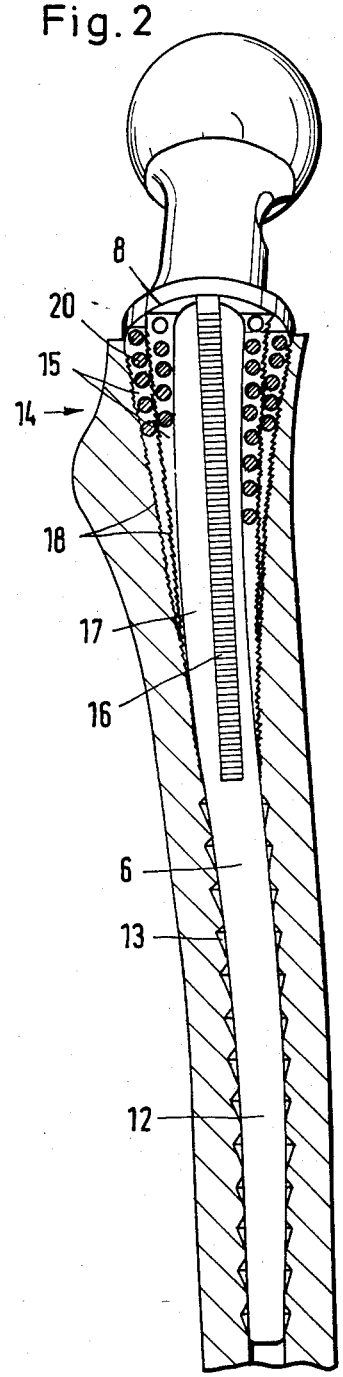

FEMORAL HIP PROSTHESIS

The invention relates to a femoral hip joint prosthesis with a stem which is intended for anchorage without cement in the femur and the proximal end section of which, in order to substantially fill the spongy part of the femur, is greatly thickened in the trochanteric region thereof, as compared with its distal section.

In the region of the femur body distal from the trochanters, the hard outer layer of the bone, namely the croticalis, is relatively thick and the medullary channel is thin. In this region, a prosthesis stem can be anchored relatively securely, because force transmission, directly or via the intermediary of bone cement, from the prosthesis to the corticalis is possible. In the proximal region of the femur, the corticalis, which widens in the shape of a funnel, is very thin, and the cross-section of the bone is essentially formed by a finely lamellar trajectory system of the spongy bone tissue which, in the transmission of force from the prosthesis, must only be subjected to substantially lower specific loadings. This region, which, for the purposes of the present description, is designated the trochanteric femur region, is located just above the lower limit of the minor trochanter. If the prosthesis is anchored in this region by the intermediary of bone cement, the form and size of the force-transmitting surface can be adequately dimensioned by the shaping of the bone cavity, rasped out before the insertion of the prosthesis, and the form of the cement body resulting from this. If, however, the anchorage is effected without bone cement, the prosthesis stem as such must make a sufficiently large force-transmitting surface available and must therefore be greatly thickened in its proximal region, and this leads to high rigidity of the stem in this region. Desirably, however, the elasticity of the stem should approach that of the bone (Z. Orthop. 1979, page 481), since uniform transmission of force is possible only in this way. Otherwise, loosening phenomena can occur due to local bone retrogression because of overloading or relieving of the bone tissue.

In the femur prosthesis disclosed by U.S. Pat. No. 2,719,522, the proximal end section, thickened in the shape of a funnel, of the prosthesis stem carries, on its medial and lateral sides, a multiplicity of flat grooves and ribs which are presumably intended to secure the prosthesis stem in the bone against rotation. The forces to be transmitted from the prosthesis stem to the bone are neither reduced in this way, nor is their transmission facilitated.

According to German Utility Model No. 81 24,912, the ventral and dorsal surfaces of the prosthesis stem are covered with flat naps which, with cement-free anchorage, have the purpose of wedging the prosthesis stem in the bone and fixing it permanently. Since, however, a part of the forces originating from the weight loading by the human body must, in the trochanter region, be transmitted towards the medial side by compression and towards the lateral side by tension, it is not to be expected that these naps improve the force transmission conditions in the trochanter region, since their medially pointing surface parts are too small, as compared with the size of the medial shaft end which is mainly responsible for the transmission of the compressive forces.

According to Swiss Pat. No. 622,423, the proximal end section of the prosthesis stem is provided with raises which extend in a herringbone pattern and which are intended, when the stem is driven into the bone cavity prepared by operation, to improve the distribution of the displaced spongy bone tissue and hence to accelerate the anchorage of the stem by rapid growing-in of the bone. Evidently, they are not intended to play a role in the transmission of the forces which are directed medially in the proximal end section, and they are also hardly suitable for this purpose, because of their shape.

German Offenlegungsschrift No. 2,839,092 discloses a prosthesis stem formed as a nail which is provided with longitudinal ribs and can be driven into the bone channel and which, at least in its distal section, has a cruciform shape. In the proximal end section, there is no thickening, in projection, in the medial direction; therefore, a larger surface than in the distal part of the stem is not available for transmitting the medially directed forces. Only the medially pointing rib is enlarged at the expense of the lateral rib, whereby a supporting effect to reinforce the stem as such is to be achieved; the force transmission to the bone is not improved in this way—on the contrary, the medial rib effects a deep division of the highly loaded bone tissue, located medially away from the proximal shaft section, and hence weakens it.

Nail-shaped prosthesis stems, not substantially thickened in the proximal end section, are also disclosed by U.S. Pat. Nos. 3,067,740 and 3,740,769.

This state of the art does not show any means which will be capable of improving the force transmission from the proximal end section of the prosthesis stem in the medial direction to the bone in the sense of lower specific loadings and a higher elasticity of the stem. It is therefore the object of the invention to improve the force transmission conditions in the poximal (sic) end section of the prosthesis stem.

According to the invention, this is achieved when the thickening of the prosthesis stem is made in the form of a plurality of longitudinal ribs which project from a slender stem core on the dorsal and ventral sides thereof and which face the medial side with a broad surface and have a multiplicity of perforations which are substantially closed towards the ridge of the rib.

The ribs can additionally transmit medially directed forces to the stem surface via the broad surface facing the medial side and thus reduce the specific loading of the bone tissue in this direction. The perforations in the ribs do not reduce the efficiency of force transmission, because the individual perforations, as a consequence of their multiplicity, are small and therefore retain the tissue growing into them and cause it to participate in the transmission of force. Not only the rib located medially furthest on the dorsal or ventral side of the stem participates in the force transmission in the medial direction; rather, this also applies to the next rib or ribs, because these, by their medially directed broad surfaces, have a force-transmitting effect on the bone tissue growing in between the ribs. From this tissue, the forces can be passed on, without problems, to the harder cross-sectional parts of the bone which surround the prosthesis stem, because the ribs do not effect a division of the bone tissue, since the bone tissue located between the rib (sic) is connected to, and supports, the remaining bone tissue via the multiplicity of rib perforations. In addition to their object of connecting and supporting the bone regions located on either side of a rib, the perforations have the purpose of reducing the rigidity of the ribs in the case of a bending stress on the stem, in order to increase the elasticity of the latter in this way.

Their arrangement can be selected, in accordance with known static principles, such that this aim is fulfilled in the best way. The reduction of the rigidity of the ribs is largely successful when the openings towards the ridge of the rib (that is to say the rib surface which points away from the stem) are at least partially open. However, to ensure that the ribs can not only transmit compressive forces to the tissue by their broad sides and their ridges, but can also transmit tensile forces in the region of their openings, the perforations must not, according to the invention, be completely open towards the ridges of the ribs. In the sense of the invention, they are substantially closed if a substantial part of their boundary surface, located closer to the ridges of the ribs, is closed. For example, it is possible to open all or some perforations towards the ridges of the ribs by means of a thin slit and thus to reduce the rigidity of the ribs, without losing the closed character of these perforations as a result.

Advantageously, at least one rib having perforations which are substantially closed towards the ridge of the rib is also provided on the lateral side of the stem core in the proximal end section of the prosthesis stem, which rib is intended to effect a participation of the lateral bone region near the major trochanter in the force transmission, by transmitting tensile forces from the prosthesis to this bone region. As a result, the medial bone region is relieved on the one hand and, on the other hand, the lateral bone region is largely protected from retrogression phenomena which are to be ascribed to excessive relief of forces.

According to the invention, the medial side of the proximal end section of the prosthesis stem can be substantially free from ribs, in order to prevent interference with the uniformity of the highly loaded, medially located bone region. Minor raises or depressions are not affected by this consideration.

The center axes of mutually adjacent ribs on the ventral or dorsal side of the shaft advantageously enclose, in cross-section, an angle of not more than 30° between them and, preferably, are even aligned approximately parallel to one another, in order thus to obtain an even more intimate bonding of the bone tissue, growing into the interspace, with the ribs. This does not exclude a rounded cross-section on the edge of the ribs, in order to obtain harmonic lines of force in the bone tissue. It serves the same purpose when, according to the invention, mutually adjacent ribs on the dorsal or ventral side of the stem enclose an interspace, the mean cross-sectional depth of wnich, relative to the trochanteric femur region, is at least approximately equal to its width. In fact, the mutual engagement of the stem with the bone tissue is improved in this way.

Advantageously, at least two ribs are provided in each case on the dorsal and ventral sides of the proximal end section of the stem. Particularly in the thicker stem region close to the end, even more ribs, for example three ribs, can be provided.

The clear dimensions of the perforations are advantageously not greater than about 5 mm across, and preferably not more than 3 mm, in order to make possible an intimate bonding with the bone tissue and, in particular, also a transmission of tensile forces from the stem to the bone tissue. For example, they can be formed as bores of a circular clear cross-section.

The reason for the feature of the ribs extending in the longitudinal direction of the stem is, on the one hand, that they should face the medial side with broad surfaces. On the other hand, this facilitates operation and re-operation.

An essential feature of the invention is that the cross-sectional height of the ribs is such that adaptation to differing femur dimensions is obtainable by ablation from the ridges of the ribs. For making endoprostheses having holding stems of different thickness, to be inserted into the medullary cavity of bones, the method according to the invention is such that, while using a holding stem of always the same shape and provided with projecting ribs, the different holding stems are produced by shaping the ridges of the ribs. In this way, a large number of standard sizes can be made available with the use of only a few stem blanks. Even an individual adaptation to the form of the bone receiving the prosthesis, as established by X-ray photograph, is conceivable.

The advantages of the invention are predominantly that the splitting of the stem cross-section into a plurality of ribs, on the one hand, permits a largely arbitrary sizing of the section modulus and hence an adaptation of the elasticity to that of the bone and that, on the other hand, the surface available for the bonding to the bone tissue which is existing or is growing in, is enlarged in the direction of greatest load so that firm seating of the prosthesis can be obtained. By virtue of the intimate anchorage, the spongy bone tissue growing into the interspaces of the ribs participates in the force transmission and in the nutrition of the bone.

The term ribs does not restrict the cross-sectional shape of the prosthesis parts described by this term. In general, however, it presupposes that the ribs have, at least over a substantial part of their length, a cross-sectional shape with dimensions which are larger in their main direction tending outwards from the stem core than transversely thereto.

The feature of the ribs extending in the longitudinal direction does not mean that their shape must be uninterrupted in this direction. Rather, depressions, slits or interruptions taken from the outside inwards can be advantageous for influencing their static strength. To influence their longitudinal yielding, it is also possible to envisage a honeycomb-like structure of the ribs or of their perforations. The ridge of the rib can be formed with raises and depressions, like a serration which, when the prosthesis stem is driven in, cuts its own way through.

In the case of a re-operation, it can be necessary to remove, or at least to loosen, the bone substance located between the ribs. Since the neck support can be a hindrance in this case, the prosthesis is made, according to a further feature of the invention, without a neck support or with devices for the removable fixing of a neck support.

Figure 4:
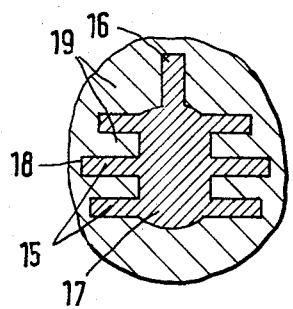
Figure 5:
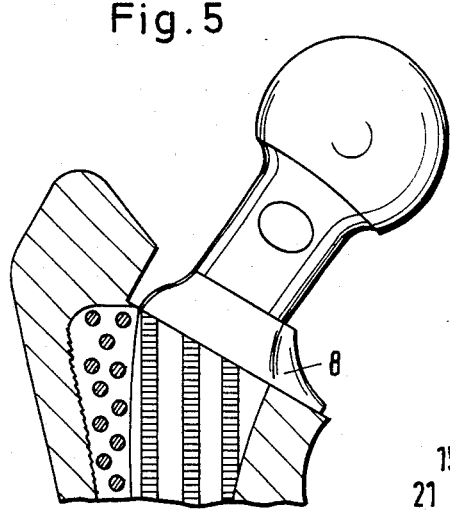
Figure 8:
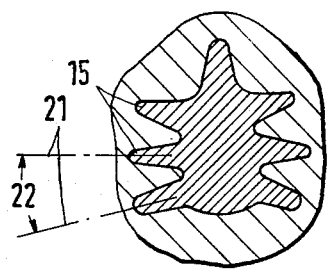
Figure 6:
Figure 7:
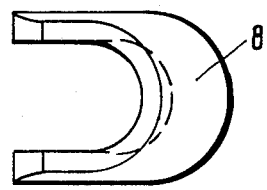
Figure 9:
Figure 10:

In the text which follows, the invention is explained in more detail by reference to the drawing which illustrates advantageous embodiment examples and in which:

FIG. 1 shows a longitudinal section in the lateral-medial plane of a femur bone with an inserted hip joint prosthesis, FIG. 2 shows a section of the same arrangement in the anterior-posterior plane, FIG. 3 shows a sectional view, corresponding to FIG. 2, with a different prosthesis shape, FIG. 4 shows a horizontal section through the bone shaft and prosthesis stem, close to the proximal shaft end, FIG. 5 shows a partial view, corresponding to FIG. 1, of a prosthesis with a removable neck support, FIGS. 6 and 7 show a sectional view and a plan view of the neck support, FIG. 8 shows a section, similar to that of FIG. 4, through another embodiment and FIGS. 9 and 10 show partial representations of ribs having different forms of perforations.

The sectional view surfaces of the femur bone 1 are shown dotted in the drawing. The medullary cavity 2 and, laterally, the major trochanter 3 and the resection surfaces 4, 5, along which the femoral neck with the condyle head has been removed, will be seen in FIG. 1. The stem 6 of the prosthesis 7, inserted without cement, is located in the scraped-out medullary cavity 2. The stem 6 is proximally closed by the neck support 8, the lower surface 9 of which rests on the resection surface 4. This is adjoined by the neck 10 with the condyle head 11. In the illustrative examples of FIGS. 1 to 3, it is assumed that all these prosthesis components consist integrally of the same material, for example forged titanium.

In its lower region 12, the prosthesis stem 6 is made with a closed surface which, for better bonding to the bone, can be provided with naps 13 of any suitable form. In this region, the medullary cavity of the bone is comparatively narrow and differs less between individuals, so that a large number of varying prosthesis forms is not required.

At the proximal end, the medullary cavity 2 widens in the region which is generally indicated by the reference numeral 14, in general in the shape of a trumpet, as assumed in FIGS. 1 and 2. However, other forms of widening also occur, for example as shown in FIG. 3. In order to avoid the necessity of making the stem 6 solid in this widened region and providing a large number of variations in form, corresponding to the individual internal shape of the corticalis, the prosthesis stem has a plurality of ribs 15, 16 which, in cross-section, project far outwards from the comparatively thin stem core 17 and some of which approach the corticalis. At least, the prosthesis cross-section determined by the ribs largely fills the spongy part of the trochanteric femur region. The depth of the ribs (main dimension from their ridge surface 18 down to the stem core 17) is greatest at the proximal end, whilst it distally vanishes gradually down to zero.

In cross-section (FIG. 4), in the given examples, six ribs 15 are arranged mutually parallel on opposite sides, whilst one rib 16 extends transversely thereto. This arrangement allows manufacture by forging. If another manufacturing process is selected, the ribs can also extend in a different arrangement. However, it is always important that at least those ribs located closest to the medial position form distinct force transmission surfaces facing in the medial direction. Over a substantial part of their length, their depth dimension is greater than their width or at least approximately equal to the latter. Between the ribs 15, 16, there are interspaces 19, in which the existing bone tissue can remain or new bone tissue can form. The ribs are provided with a multiplicity of transverse bores 20, which reduce the resisting force of the ribs to longitudinal forces and thus make the ribs more yielding. In those regions where the ribs are particularly deep, this effect is reinforced by an offset arrangement of the perforations. Moreover, bone tissue can grow into the perforations and thus improve the anchorage of the prosthesis stem in the bone and even permit the transmission of tensile forces.

The ridge faces 18 of the ribs are serrated, which is intended not only to serve for positive bonding to the bone tissue but, on insertion into the tubular bone, can have an effect which resembles the functioning of a reamer and which, with a correspondingly tight preparatory treatment of the bone cavity, ensures that the ridge faces of the ribs are in contact with the bone tissue, without gaps.

According to the direction of the insertion movement of the prosthesis stem into the bone, the ribs can be curved, so that the bone substance which must be removed before or during the insertion is minimized.

The force transmission in the medial direction is promoted by the extensive side faces, interacting with the bone tissue, of the ribs 15. The lateral rib 16, which, in the known arrangement, engages in the trochanter, also causes the latter to participate in the transmission of forces. Additionally, further means can be provided for the transmission of forces from the prosthesis stem or from the neck support 8 to the lateral regions of the bone.

The longitudinal yielding of the ribs can be enhanced by lateral incisions. For example, it is provided in FIG. 9 that all or some of the holes 20 are connected by a slit to the rib surface 18. This reduces the section modulus of the upper part of the prosthesis substantially to that of the stem core 17. Compression movements and stretching movements, which, for a given bending moment, can resemble those of the natural bone substance, then occur on the outer faces 18 of the ribs.

According to FIG. 10, it is provided that the perforations are formed and arranged in the manner of a honeycomb, in such a way that they are separated by thin bridges which run obliquely to the longitudinal direction of the stem and can be sized such that the desired elasticity of the stem is obtained.

Whilst the neck support 8 in FIGS. 1 to 3 was assumed to be integral with the prosthesis stem, it consists, in the case of FIGS. 5 to 7, of a separate horseshoe-shaped part which, after the insertion of the prosthesis, can be joined to the latter firmly but releasably, in a manner which is not shown. In the case of a re-operation, this facilitates access to the rib interspaces 19 for undoing the bond to the bone tissue at those points.

It will be seen that prostheses of different rib shape can be produced from the same blanks by correspondingly different milling of the ridges of the ribs. For example, the illustrative embodiments of FIGS. 2 and 3 can also be produced from the same blanks. It is no disadvantage if some of the perforations are completely opened by the ablation of material from the ridges of the prosthesis, provided only that other perforations are preserved which are substantially closed towards the ridge of the rib and can thus transmit tensile forces between the prosthesis and the surrounding bone material by acting on the bone material which has grown into them.

FIG. 8 shows a prosthesis cross-section in which the center axes 21 of adjacent ribs 15 mutually enclose a narrow angle 22 which is smaller than 30°. The space 19 formed between them represents—in the same way as in the example of FIG. 4—a chamber in which bone tissue can anchor itself.

It is to be regarded as an advantage of the prosthesis according to the invention that the rib ridges 18, which, after the operation, should be in direct contact with bone tissue, allow an initially sufficient force transmission under moderate loading. The full load-bearing capacity is established with the growing of the bone into the rib interspaces 19.

The mean widths of the interspaces should in general be not less than 2 mm. A mean width of about 3 mm has proved to be advantageous.

I claim:

1. A femoral hip joint prosthesis comprising:
   a slender stem core (17) having a proximal end section for engaging a trochanteric region (14) of a femur (1) and having a distal section (12) for extending into a medullary cavity; and
   a plurality of longitudinal ribs (15) projecting from said stem core and extending along said proximal end section on each of dorsal and ventral sides of said stem core, each of said ribs having a ridge surface (18) opposite said stem core to engage surrounding bony tissues, each of said ribs having a broad surface extending between said stem core and said ridge surface and facing a medial side of said femur;
   each of said ribs defining a multiplicity of perforations (20) extending through said broad surface.

2. A prothesis as claimed in claim 1, further comprising at least one rib (16) having perforations (20) on a lateral side of said stem core.

3. A prosthesis as claimed in claim 1, wherein a medial side of said stem core is free from ribs.

4. A prosthesis as claimed in claim 1, wherein each rib is bisected by a center plane extending outward from said stem core and the center planes of mutually adjacent ribs on one of said ventral and dorsal sides of said stem core enclose, in cross-section, an angle of not more than 30° between them.

5. A prothsis as claimed in claim 4, wherein said ribs (15) are aligned approximately parallel to one another.

6. A prosthesis as claimed in claim 4, wherein mutually adjacent ribs (15) on said dorsal or ventral side of said stem core enclose an interspace (19), the mean cross-sectional depth of which in said trochanteric region is at least approximately equal to its width.

7. A prosthesis as claimed in claim 4, wherein at least two ribs (15) are provided in each case on said dorsal and ventral sides of said stem core.

8. A prosthesis as claimed in claim 7, wherein three ribs are provided in each case on said dorsal and ventral sides of said stem core.

9. A prosthesis as claimed in claim 1, wherein said perforations (20) have a means diameter of not more than 5 mm.

10. A prosthesis as claimed in claim 9, wherein said mean diameter is not more than 3 mm.

11. A prosthesis as claimed in claim 1, wherein said perforations (20) are formed as bores of a circular cross-section.

12. A prosthesis as claimed in claim 1, wherein the cross-sectional height of said ribs is such that adaptation to differing femur dimensions is obtainable by ablation from said ribs.

13. A prosthesis as claimed in claim 1, further comprising a removable neck support (8) coupled to said proximal end section of said stem core and adapted to engage a patient's hip.

14. A method for making endoprostheses having holding stems of different thickness, to be inserted into the medullary cavity of bones, comprising:
   providing a stem comprised of a stem core having a proximal end section for engaging a trochanteric region of a femur and having a distal section for extending into a medullary cavity, said stem core having a plurality of longitudinal ribs projecting from said stem core and extending along said proximal end section on each of dorsal and central sides of said stem core, each of said ribs having a ridge surface opposite said stem core to engage surrounding bony tissues, each of said ribs having a broad surface extending between said stem core and said ridge surface and facing a medial side of said femur;
   shaping said ridge surface to vary the distance said ribs project from said stem core, thereby varying the thickness of said stem.

15. A prosthesis as claimed in claim 1 wherein at least one of said ribs defines a plurality of slits, each said slit extending from an outer surface of said ridge to one of said perforations.

16. A femoral hip joint prosthesis comprising:
   a slender stem core (17) having a proximal end section for engaging a trochanteric region (14) of a femur and having a distal section (12) for extending into a medullary cavity;
   a plurality of longitudinal ribs (15) projecting from said stem core and extending along said proximal end section on each of dorsal and ventral sides of said stem core, each of said ribs having a ridge surface (18) opposite said stem core to engage surrounding bony tissues, each of said ribs having a broad surface extending between said stem core and said ridge and facing a medial side of said femur;
   each of said ribs defining a multiplicity of perforations (20) extending through said broad surface; and
   at least one of said ribs defining a plurality of slits, each said slit extending from said ridge surface to one of said perforations.

17. A femoral hip joint prosthesis for anchoring free of cement in a femur, comprising:
   a stem core (17) having a proximal end section for engaging a trochanteric region (14) of a femur (1) and having a distal section (12) for extending into a medullary cavity; and
   a plurality of longitudinal ribs (15) projecting from said stem core and extending along said proximal end section on each of dorsal and ventral sides of said stem core, each of said ribs having a ridge surface (18) opposite said stem core to engage surrounding bony tissue, each of said ribs having a broad surface extending between said stem core and said ridge and facing a medial side of said femur;
   said broad surfaces of adjacent ribs facing each other defining an interspace and being adapted to engage the bone tissue contained in such interspace for the transmittance of medially directed forces.

18. The prosthesis of claim 17 wherein said ridge surfaces of said ribs define an outer contour of said prothesis which is thicker than an outer contour of said distal section of said prosthesis.

19. The prosthesis of claim 17 wherein said broad surfaces of said ribs define a plurality of perforations and a plurality of slits, each of said slits extending from one of said perforations to said ridge surface of said rib.

20. The prosthesis of claim 17 wherein said ridge surfaces are toothed.

21. The prosthesis of claim 17 wherein said ribs are approximately parallel to one another.

22. The prosthesis of claim 17 wherein said ribs have a width and a depth which are approximately equal over a substantial portion of a length of said ribs.

* * * * *